(12) United States Patent
Harms et al.

(10) Patent No.: US 10,434,757 B2
(45) Date of Patent: Oct. 8, 2019

(54) METHOD OF MANUFACTURING A DRUG DELIVERY DEVICE BODY

(75) Inventors: Michael Harms, Frankfurt am Main (DE); Steffen Raab, Frankfurt am Main (DE); Uwe Dasbach, Frankfurt am Main (DE); Udo Stauder, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 1204 days.

(21) Appl. No.: 13/258,164

(22) PCT Filed: Mar. 31, 2010

(86) PCT No.: PCT/EP2010/054346
§ 371 (c)(1),
(2), (4) Date: Dec. 6, 2011

(87) PCT Pub. No.: WO2010/115820
PCT Pub. Date: Oct. 14, 2010

(65) Prior Publication Data
US 2012/0071834 A1    Mar. 22, 2012

Related U.S. Application Data

(60) Provisional application No. 61/169,867, filed on Apr. 16, 2009.

(30) Foreign Application Priority Data

Mar. 31, 2009 (EP) .................................... 09004669

(51) Int. Cl.
*B32B 37/12*    (2006.01)
*A61M 5/31*    (2006.01)

(52) U.S. Cl.
CPC ....... *B32B 37/1292* (2013.01); *A61M 5/3129* (2013.01); *A61M 2205/583* (2013.01);
(Continued)

(58) Field of Classification Search
CPC ...................... B32B 37/1292; A61M 2205/60
See application file for complete search history.

(56) References Cited

U.S. PATENT DOCUMENTS 184,593 A * 11/1876 Curtice ................ B65D 1/0223
215/383
533,575 A    2/1895 Wilkens
(Continued)

FOREIGN PATENT DOCUMENTS

CA    2138528 C    12/1998
CA    2359375 A1    7/2000
(Continued)

OTHER PUBLICATIONS

European Search Report for EP Patent Application No. 09004669 dated Aug. 26, 2009.
(Continued)

*Primary Examiner* — Christopher T Schatz
(74) *Attorney, Agent, or Firm* — McCarter & English, LLP

(57) ABSTRACT

The invention relates to a method for manufacturing a drug delivery device body comprising the following steps:
At first a first part of the drug delivery device body wherein the surface of the first part of the drug delivery device body consists of at least one selected area and at least one non selected area is provided. The selected area of the drug delivery device body is a part of the contact area of the first part and a second part of the drug delivery device body to be fixed to the first part of the drug delivery device body. Subsequently a layer of an adhesive is deposited on the
(Continued)

surface of the first part; means for deposition of the adhesive only in the selected area are provided. The first part with the layer of adhesive and the second part are joined so that the layer of the adhesive is only arranged in the contact area of the first and the second part of the drug delivery device body.

16 Claims, 3 Drawing Sheets

(52) U.S. Cl.
CPC ..... *A61M 2205/60* (2013.01); *A61M 2207/00* (2013.01); *Y10T 156/10* (2015.01)

(56) References Cited

U.S. PATENT DOCUMENTS

| | | | |
|---|---|---|---|
| 1,656,260 A * | 1/1928 | Zeh | C03C 17/02 156/89.24 |
| 2,095,776 A | 10/1937 | Von Hofe et al. | |
| 2,338,887 A * | 1/1944 | Von Hofe | B65C 9/46 118/46 |
| 4,865,591 A | 9/1989 | Sams | |
| 4,915,950 A | 4/1990 | Miranda et al. | |
| 5,092,842 A | 3/1992 | Bechtold et al. | |
| 5,226,895 A | 7/1993 | Harris | |
| 5,226,896 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,378,233 A | 1/1995 | Haber et al. | |
| 5,383,865 A | 1/1995 | Michel | |
| 5,391,157 A | 2/1995 | Harris et al. | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,626,866 A | 5/1997 | Ebert et al. | |
| 5,674,204 A | 10/1997 | Chanoch | |
| 5,688,251 A | 11/1997 | Chanoch | |
| 5,807,346 A | 9/1998 | Frezza | |
| 5,820,602 A | 10/1998 | Kovelman et al. | |
| 5,851,079 A | 12/1998 | Horstman et al. | |
| 5,897,722 A * | 4/1999 | Bright | B29C 63/06 156/187 |
| 5,921,966 A | 7/1999 | Bendek et al. | |
| 5,957,896 A | 9/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,562,006 B1 | 5/2003 | Hjertman et al. | |
| 6,613,023 B2 | 9/2003 | Kirchhofer et al. | |
| 6,699,224 B2 | 3/2004 | Kirchhofer et al. | |
| 6,899,698 B2 | 5/2005 | Sams | |
| 6,932,794 B2 | 8/2005 | Giambattista et al. | |
| 6,936,032 B1 | 8/2005 | Bush, Jr. et al. | |
| 7,169,132 B2 | 1/2007 | Bendek et al. | |
| 7,241,278 B2 | 7/2007 | Moller | |
| 7,678,084 B2 | 3/2010 | Judson et al. | |
| 7,850,662 B2 | 12/2010 | Veasey et al. | |
| 8,187,233 B2 | 5/2012 | Harms et al. | |
| 2002/0052578 A1 | 5/2002 | Moller | |
| 2002/0120235 A1 | 8/2002 | Enggaard | |
| 2003/0050609 A1 | 3/2003 | Sams | |
| 2003/0054025 A1 | 3/2003 | Cantor et al. | |
| 2004/0010233 A1 | 1/2004 | Hjertman et al. | |
| 2004/0059299 A1 | 3/2004 | Moller | |
| 2004/0097883 A1 | 5/2004 | Roe | |
| 2004/0102566 A1 | 5/2004 | Forray et al. | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2005/0170170 A1 * | 8/2005 | Defrenne | C08J 7/047 428/323 |
| 2005/0209562 A1 | 9/2005 | Kim | |
| 2006/0153693 A1 | 7/2006 | Fiechter et al. | |
| 2007/0016143 A1 | 1/2007 | Miller et al. | |
| 2009/0275916 A1 | 11/2009 | Harms et al. | |

FOREIGN PATENT DOCUMENTS

| | | |
|---|---|---|
| EP | 0496141 A1 | 7/1992 |
| EP | 0897729 A2 | 2/1999 |
| EP | 0937471 A2 | 8/1999 |
| EP | 0937476 A2 | 8/1999 |
| EP | 1776975 A2 | 4/2007 |
| EP | 1923083 | 5/2008 |
| GB | 1051282 A | 12/1966 |
| WO | 93/07922 A1 | 4/1993 |
| WO | 93/24160 A1 | 12/1993 |
| WO | 99/38554 A1 | 8/1999 |
| WO | 01/10484 A1 | 2/2001 |
| WO | 02/030495 A2 | 4/2002 |
| WO | 02/092153 A2 | 11/2002 |
| WO | 03/080160 A1 | 10/2003 |
| WO | 2006/056736 | 6/2006 |
| WO | 2006/084876 A1 | 8/2006 |

OTHER PUBLICATIONS

International Search Report for PCT Patent Application No. PCT/EP2010/054346, dated Jul. 13, 2010.
International Preliminary Report on Patentability for International App. No. PCT/EP2010/054346, dated Oct. 4, 2011.
ISO—International Organization for Standarization, Pen-injectors for medical use, Part 1: Pen-injectors—Requirements and test methds. ISO 11608-1, First Edition, 32 pages, Dec. 15, 2000.
ISO—International Organization for Standarization, Pen-injectors for medical use, Part 2: Needles—Requirements and test methods. ISO 11608-2, First Edition, 18 pages, Dec. 15, 2000.
ISO—International Organization for Standarization, Pen-injectors for medical use, Part 3: Finished cartridges—Requirements and test methods. ISO 11608-3, First Edition, 22 pages, Dec. 15, 2000.
European Office Action for EP Application No. 10711906.7, dated Oct. 17, 2016.

* cited by examiner

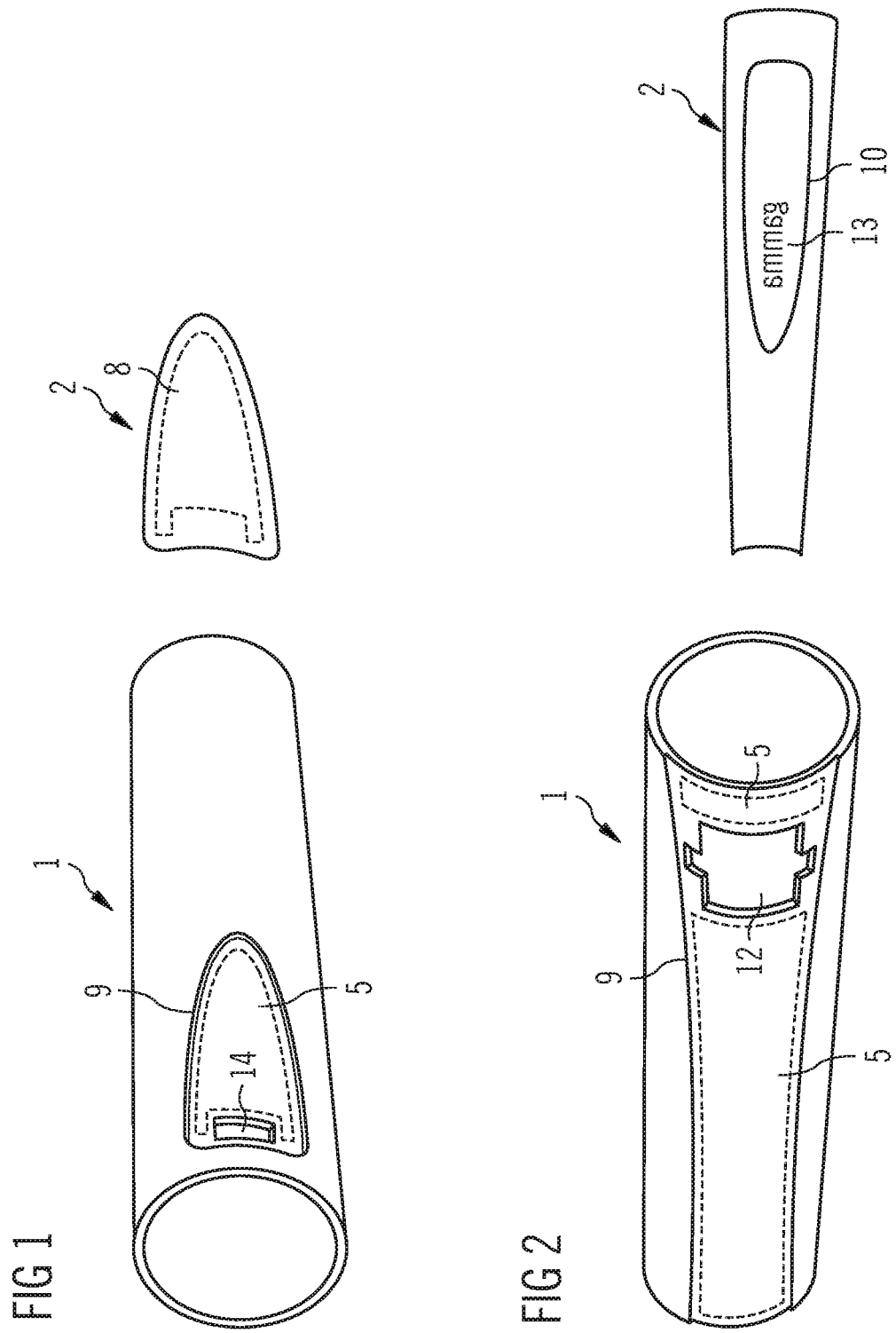

METHOD OF MANUFACTURING A DRUG DELIVERY DEVICE BODY

CROSS REFERENCE TO RELATED APPLICATIONS

The present application is a U.S. National Phase Application pursuant to 35 U.S.C. § 371 of International Application No. PCT/EP2010/054346 filed Mar. 31, 2010, which claims priority to European Patent Application No. 09004669.9 filed Mar. 31, 2009 and U.S. Provisional Patent Application No. 61/169,867 filed Apr. 16, 2009. The entire disclosure contents of these applications are herewith incorporated by reference into the present application.

FIELD OF INVENTION

The present invention relates to a method for manufacturing a drug delivery device body, particularly of a portable drug delivery device, especially a pen-type drug delivery device or injection pen.

BACKGROUND

Portable drug delivery devices are generally known for the administration of a medicinal substance or fluid, for example insulin, growth hormones or other drugs, being suitable for self-administration by a patient. A drug delivery device is especially useful in the shape of a pen, which can be handled easily and kept everywhere available. A sophisticated type of drug delivery device is constructed to be refillable and reusable many times. To secure a long life of the device, it is important to avoid damages caused during every day use.

Some drug delivery devices are constructed to deliver a plurality of different doses. One particular example of such a drug delivery device is described in EP1923083A1. The drug delivery device shown therein allows a user to activate the delivery device. For that purpose, the drug delivery device includes a drive mechanism suitable for use in pen-type injectors, where an amount of pre-set doses of a medicinal product can be administered. A needle unit can be attached to the drug delivery device for dispensing the medicinal product into a patient's body.

Necessary information about the drug delivery, the dosage or the particular drugs contained in the drug delivery device should be directly accessible by the user of the device and should therefore be visual on the body of the device. Further, with respect to patients using two different types of drugs it is helpful, if the patient has one device (for example one pen) for one type of drug and another device (for example pen) for the other type of drug. To avoid a mix-up between the two drugs, it is necessary to make the drug delivery devices distinguishable.

SUMMARY

It is an object of the present invention to provide a method for fixing a first part of a drug delivery device body to a second part of a drug delivery device body. It is a further object of the present invention to provide a method which allows to fix a part containing information or an element making the drug delivery device distinguishable to a second part of the drug delivery device body.

This object is achieved with the subject matter of the independent claims. Embodiments derive from the dependent claims.

The method for manufacturing a drug delivery device body (or a housing of a drug delivery device) according to the present invention comprises the following steps:

A) A first part of the drug delivery device is provided; this first part has one or more selected areas and one or more non-selected areas on its surface. This selected area(s) are part(s) of the contact area(s) of the first part of the drug delivery device body and a second part of the drug delivery device body which is to be fixed to the first part. In other words: the selected area is the area completely covered by the second part of the drug delivery device body after having fixed the second part to the first part of the drug delivery device body.

B) In a second step, a layer of an adhesive is deposited on the surface of the first part of the drug delivery device body; in order to allow a selective deposition of the adhesive only in the selected areas (and not in the non-selected areas), deposition means are used which particularly allow a precise deposition.

C) In a further step the first and the second part of the drug delivery device body are joined and the first part of the drug delivery device body is fixed to the second part by the adhesive. The joining of the two parts is realized in a way that after joining the layer of the adhesive is arranged in the contact area of the first and the second part of the drug delivery device body only (and does not cover any part of a non-selected area). Usually also the adhesive and/or the thickness of the layer of adhesive are selected so as to achieve a result where no part of a non-selected area is covered with adhesive.

According to the present invention, "contact area(s)" describe the area of the drug delivery device body where the second part of the drug delivery device body is fixed or is to be fixed to the first part of the drug delivery device body; the contact area comprises the selected areas and the non-selected areas on the first and the second part of the drug delivery device body as well as the layer of adhesive (and usually consists of these areas and this layer). Therefore, the contact area is the area of the first and the area of the second part of the drug delivery device body being invisible after joining of the two parts; further, the contact area comprises the area where an adhesive force fixes the first part to the second part (after joining the two parts).

A "drug delivery device body" may comprise the outer housing of the drug delivery device. Particularly, the drug delivery device and the outer housing of the drug delivery device are identical.

The method of the present invention enables an easy and an economic way to manufacture a drug delivery device body. As no adhesive is present in non-selected areas (particularly in areas where no adhesive should be present as no other part is to be fixed to these areas) negative effects on the further assembly of the drug delivery device body or the drug delivery device in general can be reduced. Further, residues of the adhesive on the outer surface of the drug delivery device can be avoided. Particularly, the joining step has no influence on the haptics of the drug delivery device (and no influence on the distinguishability of different drug delivery devices).

The means for deposition of the adhesive which allow a precise deposition of the adhesive particularly may be devices for applying the adhesive, for example printing devices or a part of these devices. Additionally of alternatively, separate tools like stencils or masks can be used as means for deposition of the adhesive. The means for deposition of the adhesive particularly allow a deposition of the adhesive so that the selected areas are completely covered with adhesive or alternatively a deposition where only a part of the selected areas is covered and the section bordering the non-selected areas is uncovered. Such a way of covering the selected and non-selected areas of the surface enables a joining step, where the area being covered with adhesive is being enlarged but not to an extent that also non-selected areas are covered with adhesive.

According to an embodiment of the invention, the adhesive is deposited on the surface of the respective part of the drug delivery device by pad printing or by spraying of the adhesive. Both methods allow the deposition of a defined amount of the adhesive and the application of a particularly thin layer of adhesive.

For both methods the adhesive can be selected from the group consisting of pressure sensitive adhesives, drying adhesives, contact adhesives, hot melt adhesives and chemical setting adhesives. Concerning chemical setting adhesives even two-component adhesives can be used, also if the adhesive is sprayed on the surface of the respective part of the drug delivery device body.

The use of pressure sensitive adhesives and drying adhesives enables a very easy method of joining. If drying adhesives are used a very quick (and economic) procedure is possible as the solvent or the dispersion medium comprised in these drying adhesives evaporates during the joining step.

If chemical setting adhesives are used, usually a higher bonding strength can be obtained. Chemical setting adhesives may, therefore, be used for parts of the drug delivery device body where high mechanical stress can occur. Concerning chemical setting adhesives in principle all known adhesives are possible: e.g. two-component adhesives and one-component adhesives are possible. The hardening of the one-component adhesives can be induced by temperature, light or ultrasonic. However, the use of (visible or UV-) light usually requires at least one transparent part of the drug delivery device body or a part of the drug delivery device body having a transparent section in the area being joined to the other part of the drug delivery device body.

In a further embodiment a mask is used for the deposition of the adhesive on the selected areas. By use of a mask, the non-selected areas can be covered; a very precise deposition of the adhesive is possible. A mask will often be used, if the adhesive is deposited on the surface of the part of the drug delivery device body by spraying as usually no adhesives will soak between the mask and the surface of the part of the drug delivery device body part.

In a further embodiment, the mask does not only cover the non-selected areas; also a part of the selected areas, particularly the part bordering the non-selected areas, is covered (for example 10 to 15% of the selected area may be covered in the section bordering the non-selected areas). If also the selected areas partially covered, a soaking of the adhesive (or solution or dispersion of the adhesive) between the mask and the part of the drug delivery device body covered by the mask may be tolerated to a certain extent. Further, such a way of covering the selected and non-selected areas of the surface enables a joining step, where the area being covered with adhesive is enlarged (for example due to the imposed pressure) but not to an extent that also non-selected areas are covered with adhesive.

In a further embodiment, bulks or spacers may be present in the selected areas. Such raised surfaces in the selected areas may be used to control the thickness of the adhesive layer (and to prevent an enlargement of the adhesive layer upon pressing the two parts of the drug delivery device body against each other).

In a further embodiment, particularly if a contact adhesive is used, a second layer of the adhesive is deposited on a second selected area on the second part of the drug delivery device body. This second selected area corresponds to the selected area of the first part of the drug delivery device body. In order to avoid the deposition of adhesive from the second layer of adhesive to non-selected areas of the first part of the drug delivery device body only the area corresponding to the selected areas of the first part of the drug delivery device body are coated with adhesive. In other words: only the area of the second part of the drug delivery device body being invisible after joining of the two parts of the drug delivery device body is (at least partially) covered with adhesive.

In a further embodiment, the first or the second part of the drug delivery device body is indicative for the drug contained in the drug delivery device. In particular, the first or the second part of the drug delivery device body may be an element of design making it easy for a user to distinguish two different drug delivery devices.

A part being indicative for the drug contained in the drug delivery device may for example provide a three-dimensional surface structure enabling a user of the drug delivery device to distinguish two different drug delivery devices by different haptics. Even for a user with impaired vision, such a drug delivery device (for example with a "structure" being Braille) provides the possibility to distinguish drug delivery devices by feeling the surface of the drug delivery device body.

Further, the (indicative) part may be colored (but can also be colored after the manufacturing process).

In a further embodiment the first or the second part of the drug delivery device body is a label, particularly a label containing a piece of information. The information may be printed or structured on the surface of the label.

In a further embodiment, the first or the second part of the drug delivery device body is a transparent cover. The cover may protect information being displayed underneath the cover. Furthermore, the transparent cover may cover a window aperture. A window aperture may be useful to allow at least one symbol representing dosage information to be visible, wherein the symbol(s) representing dosage information are changed during operation of the drug delivery device.

The transparent cover (as well as the first and the second part of the drug delivery device in general) may comprise plastics or may consist of plastics. The transparent cover, in particular, may comprise a scratch-resistant material on its outer surface to prevent or reduce damage due to gliding or scratching of the drug delivery device along a surface.

In a further embodiment, a recess is arranged in the surface of the first or the second part, wherein at least a part of the selected area of the first part (or the second part) covers at least a section of surface of the recess.

If such a recess is present in the surface, the two joined parts of the drug delivery device body can sustain more mechanical stress. If the first or the second part of the drug delivery device body is a transparent cover having a thickness being less than or at most equal to the depth of the recess, the outer surface of the transparent cover is protected from being scratched or damaged during usage or storing of the drug delivery device even more. If a mask is used in the present invention, the recess may serve as support for the exact adjustment of the mask.

In an embodiment of the drug delivery device body, it is intended for a pen-type device of elongated shape, provided at one end with an operation button. The smaller part of the two parts of the drug delivery device body, particularly a part being indicative for the drug contained in the drug delivery device or a part containing information, is located near the end of the body where the operation button is to be placed.

The term "drug", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

In another embodiment, the body is part of an assembled drug delivery device, especially an injection pen or a syringe.

According to a further aspect of the present invention, a drug delivery device body is provided. The drug delivery device body comprises a first part and a second part; the first part and the second part are joined to each other by means of a layer of an adhesive. Outside the adhesive joint no adhesive is present.

The drug delivery device according to the invention, therefore, enables an easy assembly of the whole drug delivery device; also on the outer surface of the drug delivery device body no adhesive is present and it is unproblematic to distinguish two different types of drug delivery devices, particularly due to different haptics on the surface of the drug delivery device.

Other features of examples and embodiments of the invention will become apparent from the following detailed description taken in conjunction with the accompanying drawings.

BRIEF DESCRIPTION OF THE FIGURES

FIG. 1 and FIG. 2 show a part of an embodiment of a pen-type drug delivery device body according to the invention.

Figure 3A:
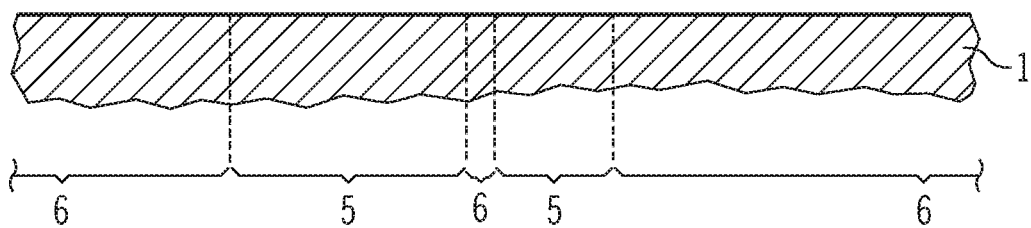
FIGS. 3A to C show in a cross-section the process of joining two parts of a drug delivery device body.

The figures show additional features that are not essential for the invention and are represented by way of illustration only. The figures are not drawn to scale.

DETAILED DESCRIPTION

FIG. 1 shows a first part 1 of an embodiment of a pen-type drug delivery device comprising a recess 9 and an aperture for secure retention of an inner part of the drug delivery device. Inside the recess 9, the selected area 5 is defined by a dashed line (for the sake of clarity of the drawing, this line rather resembles an area covered with adhesive where the section of the selected areas bordering the non-selected areas is not covered with adhesive). The dashed line does not enclose the aperture 14; therefore, adhesive deposited in the selected area 5 cannot cause any problems concerning the further assembly of the drug delivery device. The second part 2 of the drug delivery device body to be joined with the first part 1 shows a second selected area 8 corresponding to the selected area 5 of the first part 1 of the drug delivery device. Adhesive may also be deposited on the second selected area 8. After joining of the first part 1 and the second part 2 no problems are caused concerning the further assembly and the aperture 14.

FIG. 2 shows a further view of an embodiment of a pen-type drug delivery device comprising a first part of the body 1 with a recess 9 extending from one end of the pen to the other end. The recess comprises a window aperture 12 (for example to enable the display of dosage information). The dashed line inside the recess defines two separate selected areas 5 (for the sake of clarity of the drawing, these lines rather resemble areas covered with adhesive where the section of the selected areas bordering the non-selected areas is not covered with adhesive). The method according to the present invention enables a procedure where no adhesive is present in the area surrounding or extending into the window aperture 12 or jutting out on one of the ends of the first part 1. Therefore, the adhesive cannot cause any problems concerning a further assembly of the drug delivery device or concerning a complete display of dosage information. The second part 2 of the drug delivery device body comprises a transparent section 10 (which may be joined with the not transparent part of the second part 2 of the drug delivery device body according to the method of the present invention). The transparent section 10 (or the not transparent part) may contain a lettering 13 (for example the name, a trademark or information).

Figure 3B:
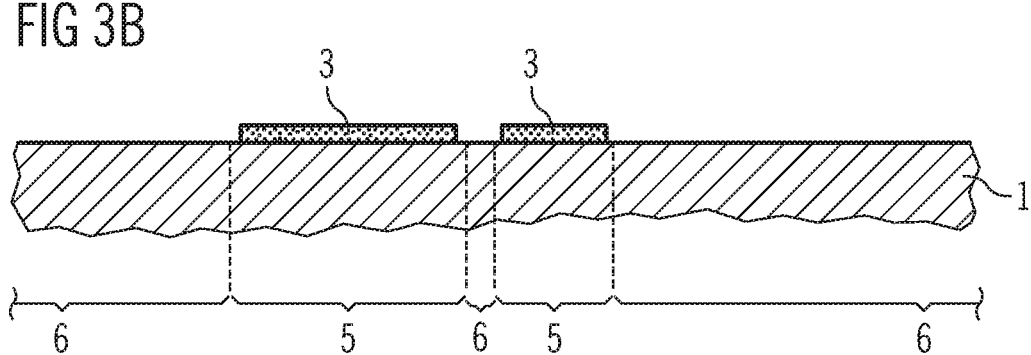
Figure 3C:
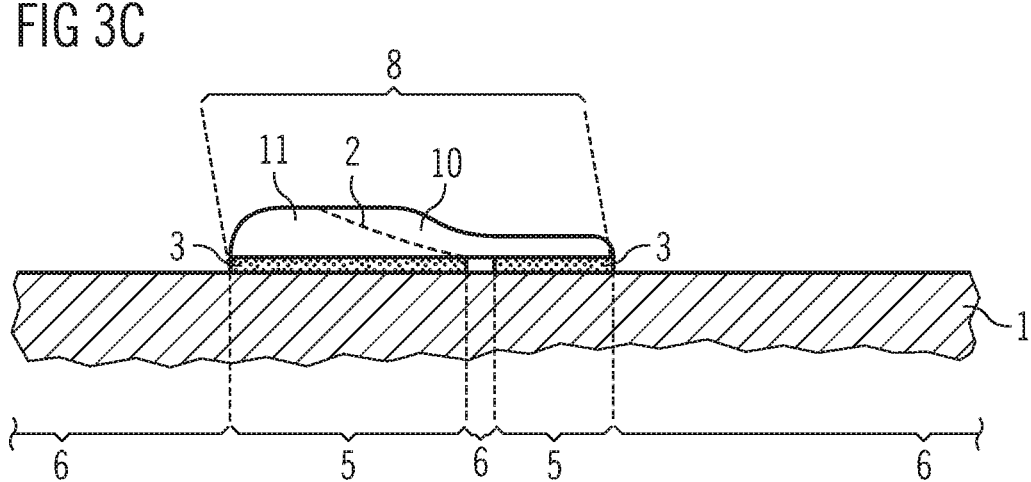

FIGS. 3A to 3C show the procedure how to manufacture a drug delivery device body according to the present invention in a cross-section. FIG. 3A shows a first part 1 of the drug delivery device body having several selected areas 5 and non-selected areas 6. FIG. 3B shows the situation after deposition of the layer of adhesive. In each of the selected areas 5 a layer of an adhesive 3 is arranged. The layer of adhesive 3 does not extend until the border between selected areas 5 and non-selected areas 6 in order to allow a certain enlargement of the film during the joining process (for example upon pressure being imposed). FIG. 3C shows the situation after joining of the first part 1 and a second part 2. The second part 2 of the drug delivery device body consists of a transparent section 10 and a non-transparent section 11. The layer of adhesives extends until the borders between the selected areas 5 and the non-selected areas 6 (for example due pressure having been imposed during the joining step). The non-selected area 6 underneath the second part 2 of the drug delivery device body, therefore, is not covered with adhesive. Therefore, the surface of the first part 1 of the drug delivery device or a not shown window aperture in the surface of the first part 1 of the drug delivery device body is visible through the transparent part 10 of the second part of the drug delivery device body 2.

Figure 4A:
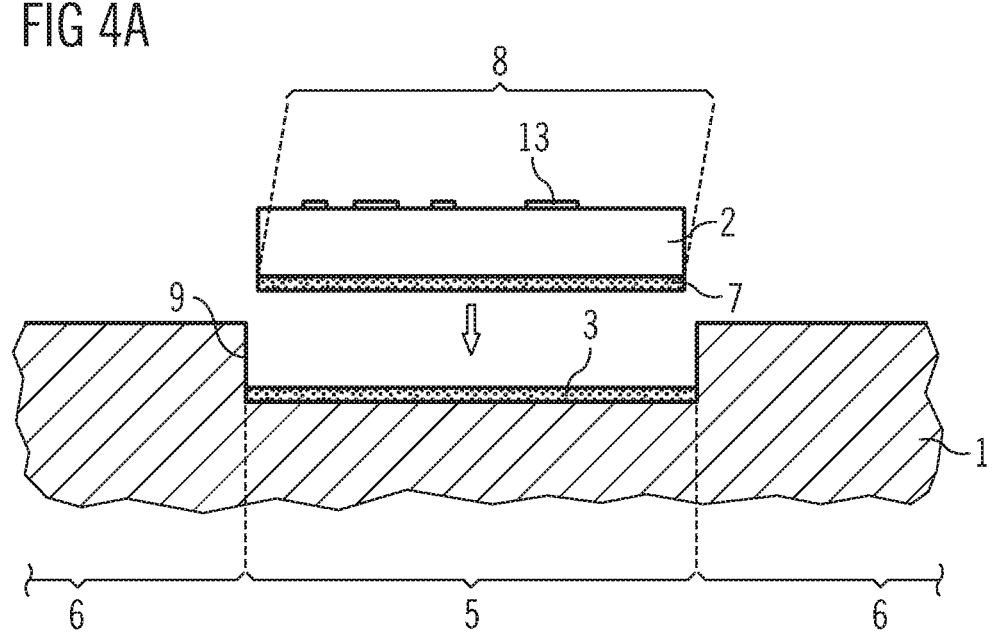
FIGS. 4A and B show in a cross-section the process of joining two parts of the drug delivery device body, wherein one part has a recess.
Figure 4B:
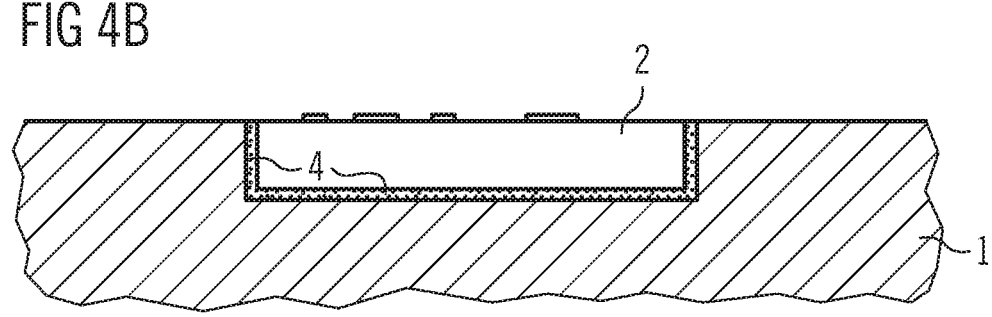

FIGS. 4A and 4B show a cross-section of the joining procedure wherein one of the parts of the drug delivery device body to be joined comprises a recess. The first part 1 of the drug delivery device body comprises a selected area 5 corresponding to the recess 9 in the first part of the drug delivery device body 1. FIG. 4A further shows a layer of an adhesive 3 deposited on the selected area 5. A second part 2 of the drug delivery device body is being joined to the first part 1. The second part 2 shows a selected area 8 corresponding to the selected area 5 of the first part 1 of the drug delivery device body. On this second selected area 8 a second layer of the adhesive 7 was deposited (FIG. 4A, therefore, shows a process where for example a contact adhesive is used; if no contact adhesive is used, usually the second layer 7 of the adhesive may be omitted). On the surface of the second part 2 facing away from the first part of the drug delivery device 1 a part of a lettering 13 (or a structure enabling a design of the device or different haptics of the device) can be seen. FIG. 4B shows the situation after joining. The adhesive is omitted for overview reasons. The adhesive does not extend the area of the adhesive joint 4.

Although the present invention and its advantages have been described in detail, it should be understood that various changes, substitutions and alterations can be made herein without departing from the spirit and scope of the invention as defined by the appended claims. Also features described in conjunction with various embodiments can be combined in different ways without leaving the scope of the invention.

The invention claimed is:

1. A method of manufacturing a drug delivery device body comprising:
   A) providing a first part and a second part of a body of a drug delivery device, the drug delivery device being a syringe or injection pen, the first part having a recess with at least one first selected area and at least one non-selected area with the non-selected area being located within the recess and outside of the first selected area, and the first part of the body having an aperture within the non-selected area of the recess, and wherein the second part is to be fixed to the first part of the drug delivery device body at the first selected area of the first part,
   B) depositing a first layer of an adhesive within the first selected area of the first part wherein deposition means for selected deposition of the first layer of adhesive only in the first selected area are provided,
   C) depositing a second layer of the adhesive on a second selected area of the second part of the drug delivery device body, wherein the second selected area corresponds to and matches in dimensions the first selected area of the first part of the drug delivery device body, and
   D) joining the first selected area to the second selected area so that the first layer of the adhesive and the second layer of the adhesive directly contact each other in a contact area of the first and the second part of the drug delivery device body only.

2. The method according to claim 1, wherein B) comprises pad printing of the adhesive.

3. The method according to claim 1, wherein the depositing in B) comprises spraying of the adhesive.

4. The method according to claim 1, wherein the adhesive is selected from the group consisting of pressure sensitive adhesives, drying adhesives, contact adhesives, hot melt adhesives and chemical setting adhesives.

5. The method according to claim 1, wherein the means for deposition of the adhesive comprises a mask covering the non-selected area.

6. The method according to claim 1, wherein the first part or the second part of the drug delivery device body is indicative for the drug contained in the drug delivery device.

7. The method according to claim 1, wherein the first part or the second part part of the drug delivery device body is an element of design.

8. The method according to claim 1, wherein the first part or the second part part of the drug delivery device body is a label.

9. The method according to claim 1, wherein the first part or the second part part of the drug delivery device body is a transparent cover.

10. The method according to claim 1, wherein the aperture of the first part is configured to align with an informational display of the drug delivery device.

11. A method of manufacturing a drug delivery device body comprising:
    A) providing a first part and a second part of a body of a drug delivery device, the drug delivery device being a syringe or injection pen, the first part having a recess with at least one first selected area and at least one non-selected area with the non-selected area being located within the recess and outside of the first selected area, and the first part of the body having an aperture within the non-selected area of the recess, and wherein the second part is to be fixed to the first part of the drug delivery device body at the first selected area of the first part,
    B) applying a mask to the first part, the mask covering at least the non-selected area,
    C) depositing a first layer of an adhesive only within the first selected area of the first part,
    D) depositing a second layer of the adhesive on a second selected area of the second part of the drug delivery device body, wherein the second selected area corresponds to and matches in dimensions the first selected area of the first part of the drug delivery device body, and
    E) joining the first selected area to the second selected area so that the first layer of the adhesive and the second layer of the adhesive directly contact each other in a contact area of the first part and the second part of the drug delivery device body only.

12. The method according to claim 11 wherein applying the mask in B) comprises using the recess as a support for precise adjustment of the mask over the non-selected area.

13. The method according to claim 11, wherein the depositing in C) comprises spraying of the adhesive onto at least a portion of the first selected area of the first part.

14. The method according to claim 11, wherein the adhesive is selected from the group consisting of pressure sensitive adhesives, drying adhesives, contact adhesives, hot melt adhesives and chemical setting adhesives.

15. The method according to claim 11, wherein the mask covers a part of the selected area bordering the non-selected area.

16. The method according to claim 15, wherein the part of the selected area bordering the non-selected area constitutes 10% to 15% of the selected area.

* * * * *

UNITED STATES PATENT AND TRADEMARK OFFICE
CERTIFICATE OF CORRECTION

PATENT NO. : 10,434,757 B2
APPLICATION NO. : 13/258164
DATED : October 8, 2019
INVENTOR(S) : Michael Harms et al.

Page 1 of 1

It is certified that error appears in the above-identified patent and that said Letters Patent is hereby corrected as shown below:

In the Claims

At Column 9, Claim 1, Line 48, insert a --,-- after the phrase "selected area of the first part".

At Column 10, Claim 7, Line 10, delete the word "part" after the phrase "the second part".

At Column 10, Claim 8, Line 13, delete the word "part" after the phrase "the second part".

At Column 10, Claim 9, Line 16, delete the word "part" after the phrase "the second part".

Signed and Sealed this
Tenth Day of March, 2020

Andrei Iancu
*Director of the United States Patent and Trademark Office*

UNITED STATES PATENT AND TRADEMARK OFFICE
CERTIFICATE OF CORRECTION

PATENT NO. : 10,434,757 B2
APPLICATION NO. : 13/258164
DATED : October 8, 2019
INVENTOR(S) : Harms et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1351 days.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*